United States Patent [19]

Ishihara

[11] Patent Number: 5,190,766
[45] Date of Patent: Mar. 2, 1993

[54] METHOD OF CONTROLLING DRUG RELEASE BY RESONANT SOUND WAVE

[76] Inventor: Ken Ishihara, 1-1-15, Chigusa, Takarazuka-shi, Hyogo, Japan

[21] Appl. No.: 684,386

[22] Filed: Apr. 12, 1991

[30] Foreign Application Priority Data

Apr. 16, 1990 [JP] Japan .................................. 2-100090

[51] Int. Cl.$^5$ .............................................. A61K 9/52
[52] U.S. Cl. .................................. 424/489; 424/491; 424/493; 424/499; 604/22
[58] Field of Search ............... 424/489, 491, 493, 499; 604/22

[56] References Cited

U.S. PATENT DOCUMENTS 4,825,851  5/1989  Cocks et al. ........................... 128/24
4,892,089  1/1990  Cocks et al. ........................... 128/24

OTHER PUBLICATIONS

"Microcapsule Drug Delivery System as Micromachine Using Resonant Ultrasound", Japan Soc. ME and BE p. 49 (Oct. 1989).
"Localization of Sonodynamic Effect for Cancer Treatment: Study of Acoustic Chemical Therapy (II)" Proceedings of the 55th Meeting of Japan Society of Ultrasonics in Medicine, pp. 683-684 (1989).
"Combination Treatment of Ultrasound and Drug on Tumor", Proceedings of the 54th Meeting of the Japan Society of Ultrasonics in Medicine, pp. 257 to 258 (1989).
"Ultrasonic Control of Drug Releasing", Japan J. Artificial Organs, vol. 13, No. 3, pp. 1205 to 1208 (1989).
Ken Ishihara et al., "New Approach to Noninvasive Manometry Based on Pressure Dependent Resonant Shift of Elastic Microcapsules in Ultrasonic Frequency Characteristics", Japanese Journal of Applied Physics, vol. 27 (1988), Supplement 27-1, pp. 125-127.

Primary Examiner—Thurman K. Page
Assistant Examiner—Amy Hulina
Attorney, Agent, or Firm—Oliff & Berridge

[57] ABSTRACT

A drug carrier carrying a drug is introduced to a diseased region of the living body while it is observed in the B mode echograms. The drug carrier is irradiated with an ultrasonic wave for strongly vibrating the drug carrier, thereby releasing the drug from the drug carrier for curing the diseased portion.

6 Claims, 1 Drawing Sheet

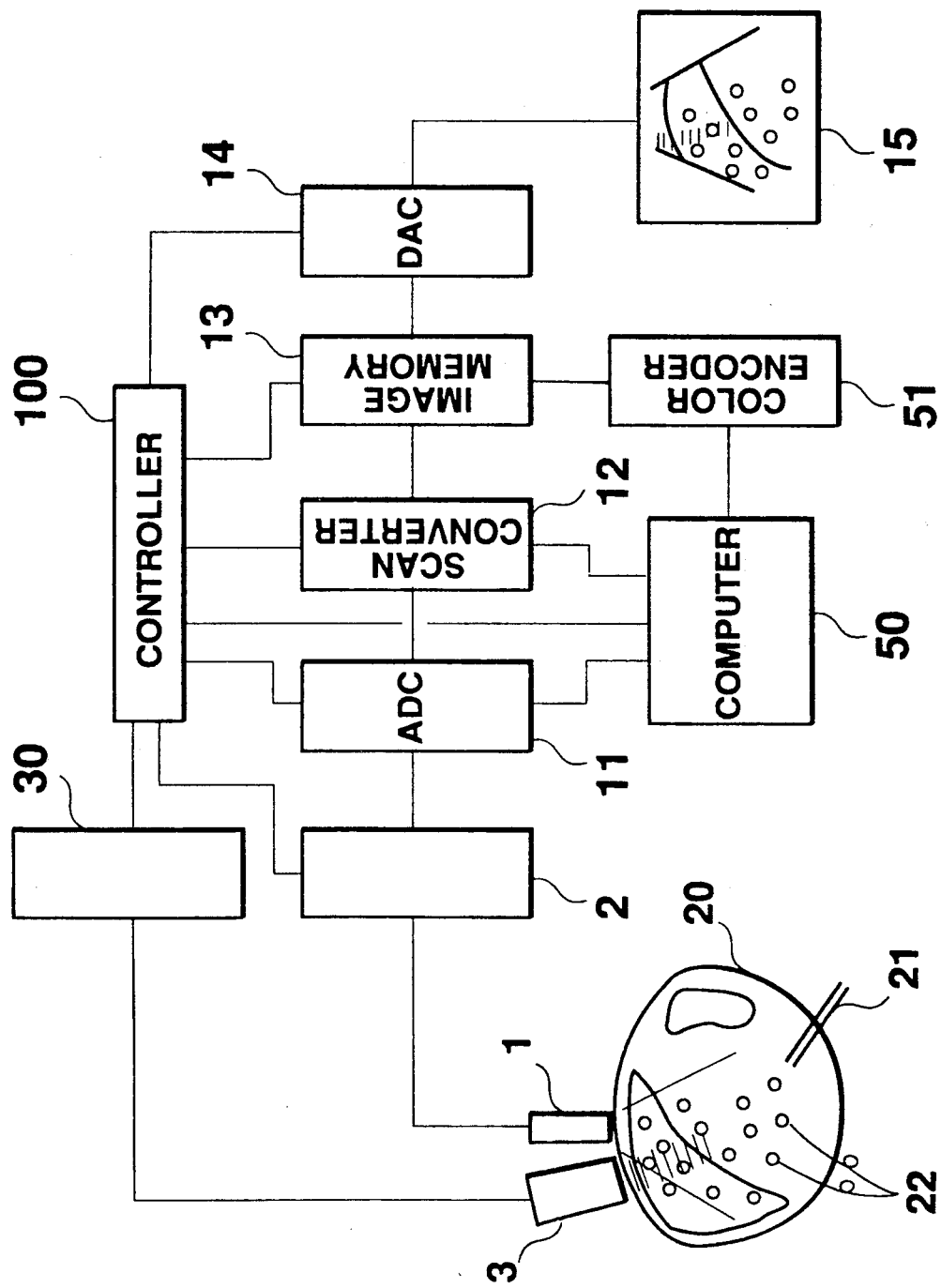

METHOD OF CONTROLLING DRUG RELEASE BY RESONANT SOUND WAVE

BACKGROUND OF THE INVENTION

1. Field of the Invention

The present invention relates to a method in a drug delivery system (hereinunder referred to as "DDS") and, more particularly, to a drug release controlling method which enables the release of any given drug on a carrier or a drug holding structure to be controlled from the outside in a non-contacting state by using a resonant sound wave (acoustic oscillatory wave including an ultrasonic wave) having a frequency corresponding to the resonance frequency of the drug carrier or the drug holding structure. This method is useful in the medical field and the like.

2. Description of the Related Art

Cancer which ranks as one of the principal death causes of Japanese and thrombosis in ischaemic heart diseases the case rate of which has recently been increasing are local lesions. However, since they are lethal, it is often inevitable to use drugs having a strong effect against such diseases even if the side effects of the drugs to the whole body are strong. Development of a method of administering a drug only to the diseased region has therefore been strongly demanded.

To meet such demand, various DDS's (drug delivery systems) for executing the maximal effective cure by drugs while suppressing the side effects by controlling the desired absorption passage, degradation rate, metabolization rate and the like in place of simply administering the drug as it is have been proposed. For example, the following techniques and systems have been proposed: (1) a technique of forming an effective drug into a prodrug or an antidrug, (2) a pharmaceutical technique such as a technique of improving a base of a long-time acting drug for oral administration and a technique of forming a drug contained in microcapsules or liposomes, (3) prevention of the long-time action and the first pass in the liver (metabolization of a drug at the first circulation in the liver after absorption) of an endermic drug, (4) what is called missile cure in which a drug is connected with a monoclonal antibody as a targeting therapy, (5) a system in which a drug is connected with a magnetic material so as to electrically induce the drug from the outside of the body and (6) a system in which a persistent pouring pump embedded in the body is used.

A comparatively similar technique to that of the present invention in the respect that an ultrasonic wave is utilized for the control of the release of a drug is reported under the title of "Ultrasonic Control of Drug Releasing" in *Jpn. J. Artificial Organs*, Vol. 13, No. 3, pp. 1205 to 1208 (1984). According to this report, a planar substrate is formed from a matrix with a drug dispersed therein and the planar substrate is heated by strong ultrasonic irradiation so as to accelerate the drug release. However, this technique does not solve the problem in the applicability to the living body.

It is conventionally known that an ultrasonic wave exerts an effect on special chemical substances themselves. For example, an alkali solution of luminol causes an especially strong chemical luminescence by ultrasonic irradiation. Although drugs having such an acoustochemical action are greatly restricted, it is reported as the result of study of the application of photodynamic therapy to an ultrasonic range that some anticancer agents such as hematoporphyrin, which is a porphyrin derivative, enhance the cytotoxicitic effect as an acoustochemical action. This is reported in "Combination treatment of Ultrasound and Drug on Tumor" in *Proceddings of the 54-th Meeting of the Japan Society of Ultraxonics in Medicine*, pp. 257 to 258 (1989), and, as a serial report, the localization of a strong ultrasonic sound field and enhancement of the cytotoxicitic effect realized by the focalization of an ultrasonic beam is described under the title of "Localization of Sonodynamic Effect for Cancer Treatment: Study of Acoustic Chemical Therapy (II)" in *Proceedings of the 55-th Meeting of the Japan Society of Ultrasonics in Medicince*, pp. 683 to 684 (1989).

None of these methods described above, however, satisfy all of the following five important conditions that the drug delivery systems are required to satisfy in the clinical application thereof: 1) that it is possible to control drug delivery so that only an organ unit or a diseased region spatially limited in the body is targeted or subjected to concentrated administration of the drug, 2) that it is possible to release or activate a drug at any time after administration, 3) that there is a method of observing the distribution state and the concentration of a drug in order to satisfy the conditions 1) and 2), 4) that the drug delivery system is applicable to any kind of drug and 5) that the drug delivery system is non-invasive. Although there are techniques which satisfy one to about three of these conditions, if any one of these conditions is unsatisfactory, the drug delivery system cannot be said to be complete as medication.

For example, a missile cure which is one of targeting therapies and in which a drug is combined with a monoclonal antibody by applying an immunological technique is thought to satisfy the above conditions. However, since cross-reaction, which is a binding of non-specific antibodies between various tissues, is considerably large, it is often difficult to satisfy the condition 1). In addition, even the pre-stage process in which the drug is combined with the antibody while keeping the activity of the drug is not easy. Even if these problems are solved, it is impossible to control the targeting of the drug after administration from the outside of the body. Furthermore, in the observation of the distribution state of the drug from the outside of the body, it is impossible to observe even the rough distribution of the drug in the body unless a substance harmful to the living body such as radioactive isotope is added to the drug.

A drug releasing method using a planar substrate with a drug applied thereto and a method of utilizing an acoustochemical action has the following defects which make the application thereof to the living body difficult.

The method of irradiating a planar substrate with a drug applied thereto with a strong ultrasonic wave so as to raise the temperature and accelerate the drug release is defective 1) in that a large planar substrate put into the body is invasive and it is impossible to form a planar substrate so smaller than the erythrocyte (not more than about 0.008 mm in major axis) as to enable intravenous injection into the vessel, and to hold planar substrates in the state in which the planes are arranged in the same direction, 2) in that since the drug releasing effect is different depending upon the angle between the projected beam of an ultrasonic wave and the planar substrate, quantitative control is difficult and 3) in that there is no drug releasing effect unless the sound pressure exceeding the value tolerable to the living body is used. According to "Ultrasonic Control of Drug Releasing" described above, in the experiment of a system in which 2.4% of methyl orange as an indicator drug was dispersed in the matrix of a planar substrate of polymethyl methacrylate, the drug release showed a high value by ultrasonic irradiation at any of the sound energy intensities of 1, 2, and 3 W/cm². However, the intensity of ultrasonic wave which is permitted by the spatial average-temporal average intensity standard for electronic scanning ultrasonic diagnostic apparatuses which is regulated by JIS is not more than 100 mW/cm² in the mode A, 10 mW/cm² in the mode B and not more than 40 mW/cm² in the mode M except for embryos, and not more than 10 mW/cm² in each mode for embryos. The permissible intensity of ultrasonic wave applied to the living body is 240 to 1,000 mW/cm². Therefore, the strong ultrasonic wave at a sound energy density of 1 to 3 W/cm² has many problems in the application to the living body.

The application of the method of utilizing an acoustochemical action to the living body is defective 1) in that since this method utilizes an acoustochemical effect on a drug itself and few drugs exhibit an ultrasonic chemical action, this method is applicable only to the limited drugs which show an acoustochemical effect, 2) in that even in the case of applying this method to the drugs which show an acoustochemical effect, a sound pressure required usually exceeds the value permissible to the living body and 3) in that since it is impossible to observe the distribution of administered drug in the body, feedback control for the optimum drug release is difficult.

SUMMARY OF THE INVENTION

Accordingly, it is an object of the present invention to eliminate the above-described problems in the related art and to provide a method satisfying all the five conditions that the drug delivery system is required to have.

The fundamental principal of the present invention is that when a drug carrier is irradiated with a sound wave having a frequency corresponding to the resonance frequency of the drug carrier, the sound energy is efficiently absorbed and the release of the drug from the drug carrier is accelerated.

The principle will now be explained from the theory of sound resonance. A gas-containing microcapsule which is used as a drug carrier has a resonance frequency corresponding to the surrounding pressure, diameter and the elasticity of the microcapsule film as a minute bubble in water. The formula of the resonance frequency of a bubble in water presented by M. Minneart is easy to understand.

$$f = \frac{1}{2\pi r} \sqrt{\frac{3kP}{\rho}} \tag{1}$$

wherein f represents a resonance frequency, r represents the radius of a bubble or a gas-containing microcapsule, k represents the ratio of the specific heat at a constant pressure and the specific heat at a constant volume of a gas and it is a constant of about 1.4 in the case of nitrogen or oxygen, P represents a pressure applied to a liquid and $\rho$ represents the specific weight of a liquid.

It is clear from this formula that as the pressure P increases, the resonance frequency f becomes high, while as the diameter increases, the resonance frequency f becomes low. This formula is an experimental and theoretical formula in the adiabatic state in which the viscosity of water and the surface tension are disregarded, but it is known that this formula is good with respect to measured values. This formula also approximately holds with respect to a gas-containing microcapsule as a drug carrier which is composed of a soft sheath of a polymer or the like. This was also confirmed by the present inventor by experiments, as was reported in Japanese Journal of Applied Physics, Vol. 27 (1988) Supplement 27-1, pp. 125 to 127 in which the relationship between the resonant frequency and the pressure of a microcapsule in water was discussed.

In order to accelerate the release of a drug, the gas-containing microcapsule as a drug carrier (hereinunder referred to simply as "gas-containing microcapsule") is irradiated with a sound wave which has a frequency corresponding to the resonance frequency of the gas-containing microcapsule in the living body. The absorption scattering produced with this irradiation is more marked than in the case of the irradiation of a sound wave having a non-resonant frequency and a large energy moves to the gas-containing microcapsule. By the large-amplitude vibration and the rise of the temperature caused by the resonance, the drug is released and targeting is realized at a much lower energy intensity than that in the case of the irradiation of a sound wave having a non-resonant frequency.

In order to examine whether or not the stable irradiation of a sound wave having the resonance frequency is possible when the pressure varies, the shift of the resonance frequency is calculated by using the formula (1). For example, when the diameter of the gas-containing microcapsule is 0.003 mm, which is a convenient size for a drug carrier used for an ordinary purpose, and the microcapsule is in a blood vessel having a pressure approximate to atmospheric pressure such as a peripheral subcutaneous vessel of a limb, the resonance frequency is 2185.78 kHz. (This resonance frequency is optimum for the present invention because it is approximate to the frequency of an ultrasonic diagnostic apparatus used in the present clinical field, the convergence of an ultrasonic beam and scanning by an ultrasonic oscillator are easy and the attenuation in the body is not excessive). Provided, in the state in which the gas is stagnant, the pressure is raised by 1 mmHg, r is reduced inversely proportional to the ⅓ power of P and the resonance frequency is changed to 2188.18 kHz. That is, it is theoretically estimated that the amount of shift of the resonance frequency with a pressure change of 1 mm Hg is 2.4 kHz. Even if it is assumed that the maximum of a change in the blood pressure of the same individual is as large as 100 mmHg, the amount of shift of confirmed by the present inventors by the experiments using gas-containing microcapsules. Thus, the resonance frequency never leaves the range of the frequency characteristics of an ordinary ultrasonic probe, so that it is ordinarily unnecessary to consider a special countermeasure to a change in blood pressure. In order to enhance the efficiency of resonance, the oscillation frequency may be changed in accordance with a change in blood pressure.

The present invention provides a method of controlling the release of a drug by a sound wave (acoustic oscillatory wave including an ultrasonic wave) by using a gas-containing elastic microcapsule as a drug carrier for selectively administering a drug to a local region and utilizing the fact that when the drug carrier is irradiated with a sound wave having a resonance frequency of the drug carrier from an ultrasonic wave generator, energy is absorbed and scattered with high efficiency.

As a means for transporting a drug to the target region, a gas-containing hollow microcapsule is used, and a microcapsule with a drug accommodated therein, a microcapsule with a drug applied or adhered to the outside thereof or a microcapsule containing a drug in the entire part or a part of the film is used as the gas-containing microcapsule carrying a drug. The film of a gas-containing microcapsule as a drug carrier need not necessarily be a solid body. Since a solvent having a large surface activity and maintaining a bubble in water and a hollow microcapsule composed of one or a plurality of monomolecular films also exhibit a resonance phenomenon, these may be used as a gas-containing microcapsule.

An ultrasonic wave transmitting and receiving means is controlled by a tomographic scanning means which can transmit and receive an ultrasonic wave having a given frequency and a given pulse waveform, and the distribution of microcapsules in the body is visualized from the difference in the pictures in the ultrasonic wave B mode which arises due to a plurality of frequency components in the vicinity of the resonance frequency of the gas-containing microcapsule. Even in the case of a microcapsule having an unknown resonance frequency distribution, the two-dimensional distribution of the frequency spectrum and the average value and the upper and lower limits of the resonance frequency are displayed and the optimal ultrasonic frequency for the release of a drug is made clear. A microcapsule shows the resonance frequency spectrum to the frequency which corresponds to the particle diameter. In microcapsules made of the same material and having different sizes, the resonance frequency becomes high in invert proportion to the diameter. In microcapsules made of different materials and having the same size, the resonance frequency becomes high in proportion to the hardness of the capsule film. The intensity distribution of the back scattering wave from the microcapsules with the attenuation due to the depth corrected is the drug carrier concentration distribution. By visualizing the distribution of the gas-containing microcapsules in the body, more accurate operation of the drug release controlling means is enabled.

The above and other objects, features and advantages of the present invention will become clear from the following description of a preferred embodiment thereof, taken in conjunction with the accompanying drawing.

BRIEF DESCRIPTION OF THE DRAWING

FIG. 1 is a block diagram of an example of an apparatus used for an embodiment of the drug release controlling method according to the present invention.

DESCRIPTION OF THE PREFERRED EMBODIMENT

A preferred embodiment of the present invention will be explained hereinunder with reference to FIG. 1. In this embodiment, it is assumed that this embodiment is applied to ordinary medical treatment, to which the present invention is considered to be most frequently applied, and that the resonance frequency of the gas-containing microcapsule is in the ultrasonic range.

FIG. 1 is a block diagram of an apparatus used for an embodiment of the present invention. The reference numeral 22 represents a gas-containing microcapsule as a drug carrier. A suspension containing the microcapsule 22 is injected into an object 20 being examined by injection or through an intravascular catheter.

The reference numeral 1 represents an ultrasonic probe for transmitting and receiving a diagnostic ultrasonic wave for measuring a picture in the ultrasonic B mode and the acoustic characteristic and the distribution of the gas-containing microcapsule in the body.

The reference numeral 2 represents an ultrasonic wave transmitting and receiving circuit, which includes a given waveform generator (which may be replaced by a pulser and a function generator or a frequency oscillator) for forming an ultrasonic beam which is transmitted from an ultrasonic oscillator provided in the probe 1 to the object 20 being examined, a transmission/reception delay circuit and a phasing circuit composed of an amplifier for amplifying a signal produced by converting the echo received from the object 20 being examined into an electric signal by the ultrasonic oscillator, a wave delay circuit for forming an ultrasonic beam of the received wave by adding the echo signals received by the ultrasonic oscillator after matching the phases thereof, an adder, etc.

The reference numeral 11 denotes an A/D converter for converting a video echo signal output from the ultrasonic wave transmitting and receiving circuit 2 into a digital signal, 12 a scan converter which repeats the operation of writing and reading the output signal of the A/D converter 11 in correspondence with the scanning line of the ultrasonic beam and supplies the output to a later-described picture memory, and 13 a picture memory.

The reference numeral 14 represents a D/A converter for generating a video signal from picture memory data through D/A conversion, and 15 a video monitor for displaying the video signal.

The reference numeral 50 denotes a computer for calculating various acoustic parameters from the digital signal output from the A/D converter 11 and extracting a plurality of scanning planes reconstructed by the acoustic parameters on a specific frequency so as to obtain a difference between the scanning planes. The computer 50 has a function of calculating the two-dimensional distribution of the frequency spectrum, the average value and the upper and lower limits of the resonance frequency of the gas-containing microcapsule, a function of discriminating the ultrasonic image of the microcapsule and the ultrasonic image of the living tissue by extracting the difference in the pictures in the ultrasonic B mode which arises due to a plurality of frequency components in the vicinity of the resonance frequency of the gas-containing microcapsule and a function of calculating the drug carrier concentration distribution from the intensity distribution of the back scattering wave from the microcapsules with the attenuation due to the depth corrected.

A resonance ultrasonic wave generator 30 is driven on the basis of the acoustic parameters or, in some cases, the known resonance frequency of the gas-containing microcapsule 22 in accordance with a command of a later-described controller 100 or by the manual operation of a doctor. The resonance ultrasonic wave generator 30 includes a given waveform generator (which may be replaced by a function generator or a frequency oscillator) for forming an optimal frequency including the resonance frequency of the microcapsule 22 in the object 20 being examined, a transmission/reception delay circuit for forming an ultrasonic beam which is transmitted to the object 20 being examined, etc. By focalizing the ultrasonic beam on the target region and irradiating the target region with the ultrasonic wave from the resonance ultrasonic wave oscillator 30, the energy of the sound wave is concentrated on the gas-containing microcapsules.

The reference numeral 51 represents a color encoder on which the display screen of the ultrasonic diagnostic apparatus and the monitor screen for drug release are superimposed. In this embodiment, the color displays of the distribution of the gas-containing microcapsules, the resonance frequency, the resonance ultrasonic beam, the sound field, etc. are superimposed with an ordinary picture in the B mode.

The reference numeral 100 represents a controller for synchronously executing and controlling a series of the above operations.

The ultrasonic transmission/reception circuit 2 and the resonant ultrasonic oscillator 30 preferably have the respective circuits independently of each other from the point of view of the interference of a high-frequency signal and ultrasonic beam scanning efficiency, but since many components are common to each other, these circuits can be constituted as one block if other conditions are satisfied.

The ultrasonic probe 1 and a resonance ultrasonic oscillation probe 3 are preferably provided independently of each other from the point of view of the interference of a signal, ultrasonic beam scanning efficiency and the formation of a sound field, but these probes can be constituted as one probe if other conditions are satisfied.

An ultrasonic oscillator for focalizing the sound wave having a frequency including the resonance frequency of a gas-containing microcapsule on the desired target region of the drug and irradiating the target region with the sound wave thereto is used as the means for controlling the drug release from the outside of the body, thereby concentrating the sound energy on the gas-containing microcapsules. As a result, the capsule film is vibrated at a large amplitude in the resonant state and the temperature of the microcapsule is raised, thereby accelerating and controlling the release of the drug carried by the gas-containing microcapsules. For this purpose, the ultrasonic oscillator may be provided with a means for varying and adjusting the oscillation frequency and the intensity of the sound wave.

The measuring means may visualize the distribution of the gas-containing microcapsules in the body by a reflecting ultrasonic diagnostic apparatus which utilizes the high reflection scattering of the ultrasonic wave due to the difference between the internal and external sound impedance ranges of the gas-containing microcapsule in the living body. Such visualization of the in vivo distribution enables more accurate operation of the drug release controlling means. Although the distribution of the gas-containing microcapsules may be measured only due to the difference in the brightness information observed in the images of the B mode echograms before and after injecting the microcapsules, more accurate evaluation is enabled by quantitatively calculating the distribution of the microcapsules by utilizing the frequency characteristics of the microcapsule. The attenuation of the ultrasonic wave in the living tissue is approximately uniform in the range of 0.5 to 1 dB/cm/MHz. On the other hand, the gas-containing microcapsule shows the attenuation characteristic which corresponds to the frequency. The attenuation factor is remarkably different depending upon the frequency in the vicinity of the resonance frequency. Therefore, if the ultrasonic frequency characteristic of the gas-containing microcapsule is known beforehand, it is possible to discriminate between the ultrasonic image of the gas-containing microcapsule and the ultrasonic image of the living tissue from the difference between the images in the B mode echograms which are composed of a plurality of frequency components. If the attenuation due to the depth is corrected, the intensity distribution of the back scattering wave corresponds directly to the drug carrier concentration distribution. A means for calculating these distributions can be provided inside or outside of the visualizing and measuring means. The ultrasonic diagnostic means as a means for measuring the distribution of the gas-containing microcapsules in the living body may be accommodated in the same apparatus as the drug release controlling means. The ultrasonic diagnostic probe may also serve as the resonant ultrasonic oscillator for controlling the drug release. It is also possible to use the means for superimposing the display screen of the ultrasonic diagnostic apparatus and the monitor screen for the resonant ultrasonic beam and the sound field for drug release control. By providing this means, it is possible to use a color display unit for displaying the distribution of the gas-containing microcapsules, the resonant ultrasonic beam and the sound filed on one screen.

The acoustic characteristic of the gas-containing microcapsule in vivo is sometimes different from that in vitro and there is a case in which the measurement of the acoustic characteristic in a specific region in the living body is required. To meet such a demand, the region in which the drug is released may be irradiated with the sound wave having a frequency including the optimum frequency for drug release which is obtained by feed backing the acoustic characteristic of the microcapsule measured. For this purpose, the apparatus used for this embodiment may be provided with a tomographic scanning means including an ultrasonic transmitting and receiving means which can transmit and receive an ultrasonic wave having a given frequency and a given pulse waveform as well as an ultrasonic wave produced by the intrinsic vibration of the piezoelectric element of an ultrasonic measuring probe, an A/D converter for converting the reception signal into a digital signal in the form of a radio-frequency (rf) signal or a video echo signal output from an ultrasonic wave receiving circuit, and a means for calculating and displaying the two-dimensional frequency spectrum distribution, and the average value and the upper and lower limits of the resonance frequency of the gas-containing microcapsule by calculating various acoustic parameters from the reflection intensity distribution, the frequency analysis and the correlation on the basis of the digital signal in the real time or at a given time after storing the digital signal, extracting a plurality of images of the scanning planes which are reconstructed by the acoustic parameters on a specific frequency and obtaining the difference between the images of the scanning planes.

Since the known devices can be used as the ultrasonic probe 1, the resonant ultrasonic oscillation probe 3, the ultrasonic wave receiving circuit 2 and the resonance ultrasonic wave generator 30, which are components of the apparatus used for this embodiment, the drug carrier which is characteristic of the present invention will now be explained.

In the present invention, appropriate production, selection and use of a gas-containing microcapsule as a drug carrier set forth in Claim 2 is preferred. As a drug carrier, however, it is also possible to select or product and use a microcapsule or a particle containing a liquid/sol which has an acoustic impedance greatly different from the acoustic impedance of the ambience in which the drug is released and having acoustic characteristics such as the resonance frequency and the scattering/absorbing characteristics which facilitate the use of the drug carrier in the ambience in which the drug is released.

In the case of adopting a matrix with the drug mixed therewith is used as the coating applied to the outside of the film of the gas-containing microcapsule, the microcapsule may be used as it is as the drug carrier for the present invention. As one of a preferred method of improving the accuracy of the control of drug release, the film of the microcapsule may be coated with a thin film the drug transmittance of which can be adjusted (even if non-selectively) by physical or chemical factors such as ultrasonic irradiation, a microwave or the in vivo environment.

It is preferable that the size of the gas-containing microcapsule is appropriately larger than the diameter of the capillary so as to serve as an embolus for the region of a desired size. It is considered that when the microcapsule which serves as the embolus is irradiated with a resonant ultrasonic wave, not only is the drug release accelerated but also the thermotherapic effect is enhanced, thereby exerting the synergistic effect on the cure of cancer or the like. By the use of the gas-containing microcapsule as the embolus, even if non-resonant sound wave is used, the thermotherapic effect is also displayed although the effect is lessened.

If a microcapsule having a diameter of not more than about 0.008 mm, which is the size of an erythrocyte which can pass the capillary in the body without any trouble, it is possible to transmit the suspension of the gas-containing microcapsule to the whole body or any desired local region by injection. When the super-selective local administration of a drug is required at the cost of the non-invasive administration, which is characteristic of the present invention, the microcapsule may be introduced to the local region through an intravascular catheter. If the microcapsule is positively required to serve as an embolus as in the case of the embolus therapy for cancer, the diameter of the gas-containing microcapsule is set at more than about 0.015 mm and the suspension of the gas-containing microcapsule may be selectively transmitted to any desired local region through an intravascular catheter or the like.

If the gas-containing microcapsules are accurately selected by the particle diameter or the resonance frequency itself in order to obtain a sharp peak of the resonance frequency on the frequency spectrum, they are easy to handle both by the drug release controlling means and by the drug distribution calculating means. However, when the selection is difficult, the drug release controlling means and the drug distribution calculating means may cope with the microcapsules on the assumption that the resonance frequencies of the respective microcapsules are distributed in a wide frequency range which corresponds to the particle diameter distribution.

The drug carrier as the means for transporting a drug to a desired target position or the structural means for holding a drug may be a fine particle or a specific structure other than a gas-containing microcapsule so long as it has a sharp acoustic resonance.

As for the safety for the living body into which the gas-containing microcapsules are injected, the suspension of a minute bubble has already been clinically intravascularly injected as a contrast medium for ultrasonic diagnosis and it is known to be safe like a conventional diagnostic reagent. In addition, no side effects have been reported which are produced by even direct injection of a sufficient amount of suspension of a minute bubble into the coronary artery for visualizing the blood stream in the myocardium of the heart, which is one of the organs having a low degree of tolerance in ischemia. It is therefore considered that the use of a minute bubble or a gas-containing microcapsule having a diameter of less than about 0.015 mm does not produce gas embolus and, hence, it is safe unless it is used in a medically irrationally large amount. In U.S.A, a gas-containing hollow microcapsule which is made of albumin (Albunex: registered trademark) and which is stable for more than several months has been developed and is now in clinical study. In Japan, it has also been in clinical study since 1989 and according to a progress report, serious side effects were not produced even by intravenous use of a sufficient amount of Albunex for a contrast medium for the right and left ventricles.

In this embodiment, a matrix formed by mixing 5-FU with Albunex (registered trademark) having a diameter of 0.006 mm was irradiated with an ultrasonic wave of 1.5 to 2 MHz at an intensity of 200 mW/cm$^2$. As a result, 5-FU was released in the living body.

The present invention is most promising in the medical use but it is also considered to be useful in the fields of industry, agriculture, forestry and fishery.

The present invention satisfies all the conditions that the drug delivery system are required to satisfy in the clinical application thereof: 1) that it is possible to control drug delivery so that only an organ unit or a diseased region spatially limited in the living body is targeted or subjected to concentrated administration of the drug, 2) that it is possible to release or activate a drug at any time after administration, 3) that there is a method of observing the distribution state and the concentration of a drug in order to satisfy the conditions 1) and 2), 4) that the drug delivery system is applicable to any kind of drug and 5) that the drug delivery system is non-invasive.

In addition, when a gas-containing microcapsule is used, since a gas having a greatly different acoustic impedance from that of water, which is the main ingredient of the living body, is absorbed therein, an ultrasonic energy absorbed by the capsule film, which is the interface of the gas and the water, is so large that the sensitivity of the microcapsule is greatly improved even by use of a non-resonant ultrasonic wave. Furthermore, if a resonance frequency which depends on the diameter, material and the film thickness of the gas-containing microcapsule is adopted, the concentration of the sound energy is further improved, so that it is possible to control the drug release at an intensity of an ultrasonic wave which does not affect the living body.

The merit of a gas-containing microcapsule used as a drug carrier is that it is possible to set an optimum resonance frequency by selecting the film material and the particle diameter of the gas-containing microcapsule, and that it is possible to control drug release while passing the microcapsule in the capillary or forming an embolus in a medium or small blood vessel. It has already been reported that a gas-containing microcapsule can be so designed as a drug carrier having a given resonance frequency in correspondence with the size and the material thereof.

A gas-containing microcapsule serves as a strong contrast medium in ultrasonic tomography like a minute bubble, which enables the visualization of the distribution of a drug, which is quite impossible in the related art. The visualized drug distribution is useful for cure in clinical application of the gas-containing microcapsules. For example, it is possible to selectively heighten the concentration of a drug only at the portion affected by a cancer after intravenous administration of the drug.

Since a gas-containing microcapsule produced by an ordinary process is approximately spherical, stable measurement of a drug and drug release control are possible without depending upon the ultrasonic irradiation angle.

A drug delivery system utilizing the resonance phenomenon of a gas-containing microcapsule is characterized in that the optimal external, non-invasive and spatial control of the concentration of the drug is enabled physically and dynamically, while in a conventional chemical drug delivery system, in which a drug is released in accordance with the time schedule programmed in advance, even control of spatial distribution is impossible.

While there has been described what are at present considered to be a preferred embodiment of the invention, it will be understood that various modifications may be made thereto, and it is intended that the appended claims cover all such modifications as fall within the true spirit and scope of the invention.

What is claimed is:

1. A method of controlling a release of a drug from a drug carrier or drug holding structure comprising the steps of: measuring the acoustic characteristics of a drug carrier or drug holding structure in the region in which a drug is to be released in order to calculate the resonance frequency of said drug carrier or drug holding structure and irradiating said drug carrier or drug holding structure having a sharp acoustic resonance with a sound wave having a frequency including the resonance frequency of said drug carrier or drug holding structure in said region thereby controlling the release of said drug from said drug carrier or drug holding structure.

2. The method of controlling the release of a drug according to claim 1, which further comprises administering said drug carrier or drug holding structure into a living body prior to irradiating it with a sound wave.

3. The method of controlling the release of a drug according to claim 2, further comprising the step of observing the distribution of said drug carriers in the living body by ultrasonic tomography.

4. The method of controlling the release of a drug according to claim 2, further comprising the steps of situating said drug carrier or drug holding structure in the region of the living body in which said drug is to be released in order to calculate the resonance frequency prior to generating a sound wave having a frequency which includes the resonance frequency of said drug carrier or drug holding structure.

5. The method of controlling the release of a drug according to claim 1, wherein said drug carrier is a microcapsule made of albumin, and said drug is released from said drug carrier by irradiating said microcapsule with a resonant ultrasonic wave of 1.5 to 2.0 MHz.

6. The method of controlling the release of a drug according to claim 1, wherein said drug carrier is a hollow microcapsule which contains a gas therein and said hollow microcapsule is used in a liquid, in a sol or in a living body.

* * * * *